(12) United States Patent
Bogan, Jr. et al.

(10) Patent No.: US 6,700,029 B2
(45) Date of Patent: Mar. 2, 2004

(54) PROCESSES FOR THE PREPARATION OF OLEFINS, UNSATURATED CARBOXYLIC ACIDS AND UNSATURATED NITRILES FROM ALKANES

(75) Inventors: Leonard Edward Bogan, Jr., Hatfield, PA (US); Anne Mae Gaffney, West Chester, PA (US); Scott Han, Lawrenceville, NJ (US); Michele Doreen Heffner, Chalfont, PA (US); Ruozhi Song, Wilmington, DE (US); Donald Lee Zolotorofe, Ivyland, PA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 10/307,780

(22) Filed: Dec. 2, 2002

(65) Prior Publication Data

US 2003/0109749 A1 Jun. 12, 2003

Related U.S. Application Data

(60) Provisional application No. 60/336,582, filed on Dec. 4, 2001.

(51) Int. Cl.[7] .............................................. C07C 5/333
(52) U.S. Cl. ....................................................... 585/663
(58) Field of Search ......................................... 585/663

(56) References Cited

U.S. PATENT DOCUMENTS

| | | | |
|---|---|---|---|
| 4,148,757 A | | 4/1979 | Brazdil et al. |
| 4,212,766 A | | 7/1980 | Brazdil et al. |
| 4,260,822 A | | 4/1981 | Krieger et al. |
| 5,146,034 A | | 9/1992 | Morales et al. |
| 5,198,580 A | | 3/1993 | Bartek et al. |
| 5,281,745 A | | 1/1994 | Ushikubo et al. |
| 5,380,933 A | | 1/1995 | Ushikubo et al. |
| 5,430,209 A | * | 7/1995 | Agaskar et al. ............. 585/315 |
| 5,877,377 A | | 3/1999 | Golunski et al. |
| 6,043,185 A | | 3/2000 | Cirjak et al. |

FOREIGN PATENT DOCUMENTS

| | | |
|---|---|---|
| EP | 0602864 A1 | 6/1994 |
| EP | 0630879 B1 | 12/1994 |
| EP | 0637578 A1 | 2/1995 |
| JP | 6-228073 | 8/1994 |
| JP | 7-53448 | 2/1995 |
| JP | 2000-37623 | 2/2000 |
| WO | WO 9829365 | 7/1998 |
| WO | WO 00/09260 | 2/2000 |
| WO | WO 00/14180 | 3/2000 |
| WO | WO 00/29106 | 5/2000 |

OTHER PUBLICATIONS

Catalysis Letters 38 (1996) 181–188, C. Yokoyama, et al. Platinum–tin and platinum–copper catalysts for autothermal oxidative dehydrogenation of ethane to ethylene.
Applied Catalysis A: General 208(2001) 99–110.
Applied Catalysis A: General 207 (2001) 421–431.
Applied Catalysis A: General 211 (2001) 123–130.
Applied Catalysis A: General 181 (1999) 63–69.
J. Catalysis 191, 12–29(2000).
J. Catalysis 158, 452–476(1996).
J. Catalysis 192, 128–136(2000).
J. Catalysis 187, 410–418(1999).
Catalysis Today 28, 139–145 (1996).
Catalysis Today 24, 327–333 (1995).
Catalysis Today 62, 91–99 (2000).
D.W. Flick, et al.—"Oxidative Dehydrogenation Over Promoted Chromia Catalysts At Short Contact Times"; Studies in Surface Science and Catalysis, pp. 779–784 (2000).
Stanislaw Golunski, et al.—"Lowering the Operating Temperature of Selective Oxidation Catalysts"; Chem. Commun., 2000, 1593–1594.
M. Baerns, et al.—"Alkanes as Substitutes for Alkenes in the Manufacture of Petrochemicals–A Continuing Challenge of the Presence and the Future"; DGMK Conference Chances for Innovative Processes at the Interface Between Refining and Petrochemistry, Berlin, 2002, pp. 61–79.

* cited by examiner

Primary Examiner—Joseph K. McKane
Assistant Examiner—Robert Shiao

(57) ABSTRACT

Improved processes for the preparation of olefins, unsaturated carboxylic acids and unsaturated nitrites involve the use of dehydrogenation catalysts suitable for the conversion of alkanes to alkenes and catalysts suitable for the conversion of alkanes and/or alkenes to unsaturated carboxylic acids or unsaturated nitrites.

5 Claims, No Drawings

PROCESSES FOR THE PREPARATION OF OLEFINS, UNSATURATED CARBOXYLIC ACIDS AND UNSATURATED NITRILES FROM ALKANES

CROSS REFERENCE TO RELATED PATENT APPLICATION

This is a non-provisional application of prior pending U.S. provisional application serial No. 60/336,582 filed on Dec. 4, 2001.

The present invention relates to the oxidative dehydrogenation of alkanes for the production of olefins and, more particularly, to the use of catalyst systems comprising oxidative dehydrogenation catalysts and mixed metal oxide catalysts for the preparation of unsaturated carboxylic acids and unsaturated nitriles from alkanes.

The production of alkenes (e.g., $C_2$–$C_4$ alkenes) is most commonly accomplished by the thermal cracking of hydrocarbons. This is a process requiring large amounts of energy and tends to result in the generation of undesirable by-products (such as coke), which often have the potential to reduce reactor efficiency and require occasional shutdowns.

In recent years, it has been proposed to perform an oxidative dehydrogenation reaction with a paraffinic hydrocarbon to yield the desired alkene. Efforts in the field have been reported by a number of different groups. See, e.g., thesis entitled "Catalysts for the Oxidative Dehydrogenation of Alkanes at Millisecond Contact Times" by Dr. Derrick W. Flick (2000) and his preprint of a paper Flick, et al. "Olefins by Oxidative Dehydrogenation of Propoane and Butanes over a Promoted Chromia Catalyst Supported on a Foam Monolith". In the latter, Cu is used as a promoter. It is noted that Flick's selection of catalyst composition necessitates relatively high autothermal run temperatures, e.g., as high as 400° C. higher than desired for certain reactions. Because of the higher temperatures and relatively low efficiency catalysts, conversion of alkane is low, olefin selectivity is low, CO and $CO_2$ selectivity is high and catalyst deactivation is more rapid.

Published International Patent Application WO 00/14180 (Mar. 16, 2000), entitled "Autothermal Process for the Production of Olefins", recognizes that "[I]t would be desirable to discover a catalytic process wherein a paraffinic hydrocarbon is converted to an olefin in a conversion and selectivity comparable to, or better than, commercial thermal cracking processes. It would be desirable if the catalytic process were to produce small quantities of deep oxidation products, such as carbon monoxide and carbon dioxide. It would also be desirable if the process were to achieve low levels of catalyst coking. It would be even more desirable if the process could be easily engineered without the necessity for a large, capital intensive, and complex cracking furnace. Finally, it would be most desirable if the catalyst was stable and the catalytic support not prone to fracture." The published application does not disclose the use of reducible metal oxides promoted with Group 8 metals. Moreover, the autothermal temperatures utilized were typically high, i.e. between 800° C. and 1100° C.

S. Golunski, et al., Chem. Commun., 2000, pp 1593–1594, "Lowering the Operating Temperature of Selective Oxidation Catalysts" indicated that ". . . by incorporating palladium into oxidative dehydrogenation catalysts, a key step in the usual Mars-van Krevelen redox cycle is by-passed, which results in a decrease in operating temperature of around 200° C., as compared to the unmodified iron(III) oxide." The authors incorporated palladium into $Fe_2O_3$ and $Bi_2MoO_6$. They did not use three-dimensional catalytic forms; their contact times were long, i.e. 0.6 seconds (600 milliseconds); they did not run autothermally, i.e. they applied heat to the catalyst bed; and they prepared butadiene from butene. See also, Golunski, et al, U.S. Pat. No. 5,877,377 (Mar. 2, 1999).

Unsaturated carboxylic acids such as acrylic acid and methacrylic acid are industrially important as starting materials for various synthetic resins, coating materials and plasticizers. Commercially, the current process for acrylic acid manufacture involves a two-step catalytic oxidation reaction starting with a propene feed. In the first stage, propene is converted to acrolein over a modified bismuth molybdate catalyst. In the second stage, acrolein product from the first stage is converted to acrylic acid using a catalyst composed of mainly molybdenum and vanadium oxides. In most cases, the catalyst formulations are proprietary to the catalyst supplier, but, the technology is well established. Moreover, there is an incentive to develop a single step process to prepare the unsaturated acid from its corresponding alkene. Therefore, the prior art describes cases where complex metal oxide catalysts are utilized for the preparation of unsaturated acid from a corresponding alkene in a single step.

European Published Patent Application No. 0 630 879 B1 discloses a process for producing an unsaturated aldehyde and a carboxylic acid which comprises subjecting propene, isobutene or tertiary butanol to gas phase catalytic oxidation with molecular oxygen in the presence of (i) a catalyst composite oxide represented by the formula

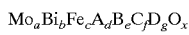

$Mo_aBi_bFe_cA_dB_eC_fD_gO_x$ wherein A represents Ni and/or Co, B represents at least one element selected from Mn, Zn, Ca, Mg, Sn and Pb, C represents at least one element selected from P, B, As, Te, W, Sb and Si, and D represents at least one element selected from K, Rb, Cs and Tl; and wherein, when a=12, 0<b≦10, 0<c≦10, 1≦d≦10, 0≦e≦10, 0≦f≦20 and 0≦g≦2, and x has a value dependent on the oxidation state of the other elements; and (ii) a molybdenum oxide which in itself is substantially inert to said gas phase catalytic oxidation to provide the corresponding unsaturated aldehyde and unsaturated carboxylic acid.

Japanese Laid-Open Patent Application Publication No. 07-053448 discloses the manufacture of acrylic acid by the gas-phase catalytic oxidation of propene in the presence of mixed metal oxides containing Mo, V, Te, O and X wherein X is at least one of Nb, Ta, W, Ti, Al, Zr, Cr, Mn, Fe, Ru, Co, Rh, Ni, Pd, Pt, Sb, Bi, B, In, Li, Na, K, Rb, Cs and Ce.

Published International Application No. WO 00/09260 discloses a catalyst for selective oxidation of propene to acrylic acid and acrolein containing a catalyst composition comprising the elements Mo, V, La, Pd, Nb and X in the following ratio:

$Mo_aV_bLa_cPd_dNb_eX_f$ wherein X is Cu or Cr or a mixture thereof, a is 1, b is 0.01 to 0.9, c is >0 to 0.2 d is 0.0000001 to 0.2, e is 0 to 0.2, and f is 0 to 0.2; and wherein the numerical values of a, b, c, d, e and f represent the relative gram-atom ratios of the elements Mo, V, La, Pd, Nb and X, respectively, in the catalyst and the elements are present in combination with oxygen.

Commercial incentives also exist for producing acrylic acid using a lower cost propane feed. Therefore, the prior art describes cases wherein a mixed metal oxide catalyst is used to convert propane to acrylic acid in one step.

U.S. Pat. No. 5,380,933 discloses a method for producing an unsaturated carboxylic acid comprising subjecting an alkane to a vapor phase catalytic oxidation reaction in the presence of a catalyst containing a mixed metal oxide comprising, as essential components, Mo, V, Te, O and X, wherein X is at least one element selected from the group consisting of niobium, tantalum, tungsten, titanium, aluminum, zirconium, chromium, manganese, iron, ruthenium, cobalt, rhodium, nickel, palladium, platinum, antimony, bismuth, boron, indium and cerium; and wherein the proportions of the respective essential components, based on the total amount of the essential components, exclusive of oxygen, satisfy the following relationships: $0.25 < r(Mo) < 0.98$, $0.003 < r(V) < 0.5$, $0.003 < r(Te) < 0.5$ and $0.003 < r(X) < 0.5$, wherein $r(Mo)$, $r(V)$, $r(Te)$ and $r(X)$ are the molar fractions of Mo, V, Te and X, respectively, based on the total amount of the essential components exclusive of oxygen.

Published International Application No. WO 00/29106 discloses a catalyst for selective oxidation of propane to oxygenated products including acrylic acid, acrolein and acetic acid, said catalyst system containing a catalyst composition comprising $$Mo_aV_bGa_cPd_dNb_eX_f$$

wherein X is at least one element selected from La, Te, Ge, Zn, Si, In and W, as 1, b is 0.01 to 0.9, c is >0 to 0.2, d is 0.0000001 to 0.2, e is >0 to 0.2, and f is 0.0 to 0.5; and wherein the numerical values of a, b, c, d, e and f represent the relative gram-atom ratios of the elements Mo, V, Ga, Pd, Nb and X, respectively, in the catalyst and the elements are present in combination with oxygen.

Japanese Laid-Open Patent Application Publication No. 2000-037623 discloses a method for producing an unsaturated carboxylic acid comprising subjecting an alkane to a vapor phase catalytic oxidation in the presence of a catalyst having the empirical formula $$MoV_aNb_bX_cZ_dO_n$$

wherein X is at least one element selected from the group consisting of Te and Sb, Z is at least one element selected from the group consisting of W, Cr, Ta, Ti, Zr, Hf, Mn, Re, Fe, Ru, Co, Rh, Ni, Pd, Pt, Ag, Zn, B, Al, Ga, In, Ge, Sn, Pb, P, Bi, Y, rare earth elements and alkaline earth elements, $0.1 \leq a \leq 1.0$, $0.01 \leq b \leq 1.0$, $0.01 \leq c \leq 1.0$, $0 \leq d \leq 1.0$ and n is determined by the oxidation states of the other elements.

Nitriles, such as acrylonitrile and methacrylonitrile, have been industrially produced as important intermediates for the preparation of fibers, synthetic resins, synthetic rubbers, and the like. The most popular method for producing such nitriles is to subject an olefin such as propene or isobutene to a catalytic reaction with ammonia and oxygen in the presence of a catalyst in a gaseous phase at a high temperature. Known catalysts for conducting this reaction include a Mo—Bi—P—O catalyst, a V—Sb—O catalyst, an Sb—U—V—Ni—O catalyst, a Sb—Sn—O catalyst, a V—Sb—W—P—O catalyst and a catalyst obtained by mechanically mixing a V—Sb—W—O oxide and a Bi—Ce—Mo—W—O oxide. However, in view of the price difference between propane and propene or between isobutane and isobutene, attention has been drawn to the development of a method for producing acrylonitrile or methacrylonitrile by an ammoxidation reaction wherein a lower alkane, such as propane or isobutane, is used as a starting material, and it is catalytically reacted with ammonia and oxygen in a gaseous phase in the presence of a catalyst.

In particular, U.S. Pat. No. 5,281,745 discloses a method for producing an unsaturated nitrile comprising subjecting an alkane and ammonia in the gaseous state to catalytic oxidation in the presence of a catalyst which satisfies the conditions:

(1) the mixed metal oxide catalyst is represented by the empirical formula $$Mo_aV_bTe_cX_xO_n$$

wherein X is at least one element selected from the group consisting of niobium, tantalum, tungsten, titanium, aluminum, zirconium, chromium, manganese, iron, ruthenium, cobalt, rhodium, nickel, palladium, platinum, antimony, bismuth, boron and cerium and, when a=1, b=0.01 to 1.0, c=0.01 to 1.0, x=0.01 to 1.0 and n is a number such that the total valency of the metal elements is satisfied; and (2) the catalyst has X-ray diffraction peaks at the following angles (±0.3°) of 2θ in its X-ray diffraction pattern: 22.1°, 28.2°, 36.2°, 45.2° and 50.0°.

Similarly, Japanese Laid-Open Patent Application Publication No. 6-228073 discloses a method of nitrile preparation comprising reacting an alkane in a gas phase contact reaction with ammonia in the presence of a mixed metal oxide catalyst of the formula $$W_aV_bTe_cX_xO_n$$

wherein X represents one or more elements selected from niobium, tantalum, titanium, aluminum, zirconium, chromium, manganese, iron, ruthenium, cobalt, rhodium, nickel, palladium, platinum, antimony, bismuth, indium and cerium and, when a=1, b=0.01 to 1.0, c=0.01 to 1.0, x=0.01 to 1.0 and n is determined by the oxide form of the elements.

U.S. Pat. No. 6,043,185 also discloses a catalyst useful in the manufacture of acrylonitrile or methacrylonitrile by the catalytic reaction in the vapor phase of a paraffin selected from propane and isobutane with molecular oxygen and ammonia by catalytic contact of the reactants in a reaction zone with a catalyst, wherein the catalyst has the empirical formula $$Mo_aV_bSb_cGa_dX_eO_x$$

where X is one or more of As, Te, Se, Nb, Ta, W, Ti, Zr, Cr, Mn, Fe, Ru, Co, Rh, Ni, Pd, Pt, B, In, Ce, Re, Ir, Ge, Sn, Bi, Y, Pr, an alkali metal and an alkaline earth metal; and when a=1, b=0.0 to 0.99, c=0.01 to 0.9, d=0.01 to 0.5, e=0.0 to 1.0 and x is determined by the oxidation state of the cations present.

Accordingly, there is a need in the art for an improved process for the oxidative dehydrogenation of alkanes to form alkenes (particularly mono-olefins), where relatively low amounts of energy are required, where contact times are relatively short, where conversions are relatively high or a combination thereof.

There is also a need in the art for efficient processes for the production of unsaturated carboxylic acids, such as acrylic acid and methacrylic acid, and unsaturated nitrites, such as acrylonitrile and methacrylonitrile, from alkanes.

Accordingly, in a first aspect, the present invention provides a method for producing an olefin, said method comprising:

a. providing a three-dimensional support structure for supporting a catalyst;

b. providing a catalyst on at least a portion of said support structure, said catalyst comprising a reducible metal oxide promoted with a Group 8 promoter metal;

c. reacting an alkane with oxygen in the presence of said supported catalyst, said reaction having a contact time of no longer than 100 milliseconds and providing a conversion rate of said alkane of at least 40%.

In a second aspect, the present invention provides a method for producing an unsaturated carboxylic acid, said method comprising:

contacting, in a reaction zone, a feed gas stream comprising an alkane with a catalyst system comprising a first catalyst component and a second catalyst component, said first catalyst component being capable of catalyzing the conversion of an alkane to a product gas comprising a corresponding product alkene and unreacted alkane, said second catalyst component being capable of catalyzing the conversion of an alkane to a product gas comprising a corresponding product unsaturated carboxylic acid and being capable of catalyzing the conversion of an alkene to a product gas comprising a corresponding product unsaturated carboxylic acid, wherein said first catalyst component is different from said second catalyst component.

In a third aspect, the present invention provides a method for producing an unsaturated carboxylic acid, said method comprising contacting, in a reaction zone, a feed gas stream comprising an alkane with a catalyst system capable of catalyzing the conversion of an alkane to a product gas comprising a product corresponding unsaturated carboxylic acid, a product corresponding alkene and unreacted alkane and being capable of catalyzing the conversion of an alkene to a product gas comprising a product corresponding unsaturated carboxylic acid;

wherein said reaction zone comprises at least two sub-zones, said sub-zones being disposed sequentially, at least one of said sub-zones being maintained at reaction conditions most favorable to the production of said product corresponding alkene, and at least one other sub-zone being maintained at reaction conditions most favorable to the production of said product corresponding unsaturated carboxylic acid; and wherein said feed gas stream passes through said sub-zones in sequential order.

In a fourth aspect, the present invention provides a method for producing an unsaturated nitrile, said method comprising:

contacting, in a reaction zone, a feed gas stream comprising an alkane with a catalyst system comprising a first catalyst component and a second catalyst component, wherein said first catalyst component and said second catalyst component may be the same or different, said first catalyst component being capable of catalyzing the conversion of an alkane to a product gas comprising a corresponding product alkene and unreacted alkane, said second catalyst component being capable of catalyzing, in the presence of ammonia, the conversion of an alkane to a product gas comprising a corresponding unsaturated nitrile and being capable of catalyzing, in the presence of ammonia, the conversion of an alkene to a product gas comprising a corresponding product unsaturated nitrile;

wherein said reaction zone comprises at least two sub-zones, said sub-zones being disposed sequentially, at least one of said sub-zones containing said first catalyst component and at least one different sub-zone containing said second catalyst component, said feed gas stream passing through said sub-zones in sequential order; and wherein ammonia is only fed to said at least one different sub-zone containing said second catalyst component.

Turning to the first aspect of the present invention, the support structure is three dimensional, i.e. has dimensions along the x, y and z orthogonal axes of a Cartesian coordinate system, and affords a relatively high surface area per unit volume. Though lower and higher amounts are possible, in one embodiment, the support structure exhibits a surface area of 0.01 to 50 $m^2/g$, preferably 0.1 to 10 $m^2/g$.

Preferably, the support structure will have a porous structure and exhibit a pore volume percent ranging from 1 to 95%, more preferably 5 to 80%, and still more preferably 10 to 50%. Thus, the support structure permits relatively high feed velocities with insubstantial pressure drop.

Further, the support structure is sufficiently strong so that it does not fracture under the weight of the catalyst, which can range up to almost 100% of the weight of the combination of the catalyst and the support structure. More preferably, however, the support structure is at least 60% of the weight of the combination. Still more preferably, it is 70 to 99.99% of the weight of the combination. Even still more preferably, the support structure is 90 to 99.9% of the weight of the combination.

The exact physical form of the support structure is not particularly important so long as it meets the above-noted general criteria. Examples of suitable physical forms include foam, honeycomb, lattice, mesh, monolith (single and multilayer), woven fiber, non-woven fiber, gauze, perforated substrates (e.g., foil), particle compacts, fibrous mat and mixtures thereof. For these supports it will be appreciated that typically one or more open cells will be included in the structure. The cell size may vary as desired, as may the cell density, cell surface area, open frontal area and other corresponding dimensions. By way of example, one such structure has an open frontal area of at least 75%. The cell shape may also vary and may include polygonal shapes, circles, ellipses as well as others.

The support structure may be fabricated from a material that is inert to the reaction environment of the catalytic reaction. Suitable materials include ceramics such as silica, alumina, silica-alumina, aluminosilicate, zirconia, titania, boria, mullite, alumina, lithium aluminum silicate, oxide-bonded silicon carbide or mixtures thereof. (Alternatively, the catalyst may be prepared so as to define the support structure itself, e.g., by "green" compacting or another suitable technique.)

The catalysts may be applied to the support structure using any suitable art-disclosed technique. For instance, the catalyst may be vapor deposited (e.g., by sputtering, plasma deposition or some other form of vapor deposition). The catalyst may be coated thereon (e.g., by wash coating a support with a solution, slurry, suspension or dispersion of catalyst). The support may be coated with a catalyst powder (i.e. powder coating). (Alternatively, where the support structure is the catalyst itself, a "green" body of catalyst may be compacted to yield the desired structure.)

The catalyst, itself, is suitable for the oxidative dehydrogenation of an alkane to form an olefin. More particularly, the catalyst for this first aspect of the invention may be a reducible metal oxide promoted with a Group 8 metal. Thus, the catalyst may be a binary, ternary, quaternary or higher order compound. The reducible metal oxide may be an oxide of a metal selected from the group consisting of Cu, Cr, V, Mn, Nb, Mo, W, Re, Ga, Ge, In, Sn, Sb, Tl, Pb, Bi, Te, As, Se, Zn, Y, Zr, Ta, Ce, Pr, Nd, Pm, Sm, Eu, Gd, Tb, Dy, Ho, Er, Tm, Yb, Lu and mixtures thereof. Preferably, the reducible metal oxide is selected from the group consisting of Cu, Cr, V, Mn, Zn and mixtures thereof. The promoter is a metal from Group 8 of the Periodic Table of the Elements (Fe, Ru, Os, Co, Rh, Ir, Ni, Pd and Pt), preferably a metal selected from the group consisting of Pt, Pd, Rh, Ir, Ru and mixtures thereof. The promoter may preferably be present in amount of from 0.0001 to 10 wt % of the catalyst composition (promoter plus reducible metal oxide), more preferably from 0.001 to 5 wt % of the catalyst composition, and still more preferably from 0.01 to 2 wt % of the catalyst composition.

For the oxidative dehydrogenation reaction of the first aspect of the present invention, the reactants are passed through a suitable reactor vessel, with or without a diluent. The reactants are provided as gases and thus, for the formation of alkenes, the reactants will include an alkane and oxygen. Optionally, the reactants may include hydrogen, water or a mixture thereof. Though other process conditions may be employed, preferably the reaction is carried out autothermally in the presence of the supported catalyst. Preferred alkanes have from 2 to 25 carbon atoms, more preferably from 3 to 8 carbon atoms, e.g., propane, butane, isobutane or mixtures thereof. A molar ratio of alkane to oxygen ranging from 0.1:1 to 4.0:1 is preferably employed.

In a preferred embodiment, the reactants are admixed or otherwise provided with a diluent. The diluent is preferably a gas at room temperature and ambient pressure; and is inert to the reaction environment under the existing reaction conditions. Suitable gases include nitrogen, argon, helium and the like. The amount of diluent is not particularly important, however, it is preferably present in an amount of from greater than 0.1 mole percent to less than 70 mole percent, based on the total feed to the reactor, when used.

The reaction temperature may range from 300° C. to 1150° C. but is preferably below 500° C. and most preferably is maintained autothermally once the reaction "lights off". The reaction pressure is not particularly important and typically may be in the range of from 1 atm abs to 20 atm abs. The contact time for the reaction is rapid and typically will be no more than 100 milliseconds, preferably no more than 50 milliseconds, more preferably no more than 20 milliseconds, still more preferably no more than 10 milliseconds, yet still more preferably no more than 5 milliseconds and most preferably no more than 2 milliseconds.

As previously mentioned, the reactants may optionally include hydrogen, water or mixtures thereof. When hydrogen is employed, the molar ratio of hydrogen to oxygen is preferably greater than 0.5:1, more preferably greater than 0.7:1, and still more preferably greater than 1.5:1. Moreover, when hydrogen is employed, the molar ratio of hydrogen to oxygen is preferably less than 3.2:1, more preferably less than 3.0:1, and still more preferably less than 2.7:1.

If water is employed, alone or in combination with hydrogen, it is present in amount of from 0.1 to 50 mole % based on the total feed to the reactor, preferably in an amount of from 1 to 30 mole %, and more preferably in an amount of from 2 to 20 mole %.

It can be appreciated from the foregoing that the process of this first aspect of the present invention efficiently produces alkenes, particularly mono-olefins, from alkanes and oxygen. High conversion and alkene selectivity are observable, even as compared with previous catalytic autothermal processes. In addition, relatively fewer deep oxidation products, such as CO and $CO_2$ are produced. The process results in substantially no coke production. The process also allows an operator to employ a relatively simple engineering design and can avoid the requirement for a large, expensive and complex furnace, as in conventional thermal cracking processes.

Because the contact time of the reactants in the process of this aspect of the invention is on the order of milliseconds, the reaction zone used in the process is substantially adiabatic and operates at high volumetric throughput. Further, the process of this aspect of the present invention permits the use of a reaction zone that measures from about one-fiftieth to about one-hundredth the size of a commercially available steam cracker of comparable capacity. The reduced size of the reactor reduces costs and greatly simplifies catalyst loading and maintenance procedures. Finally, since the process of this aspect of the present invention is exothermic, the heat produced could be harvested, if so desired, via integrated heat exchangers to produce energy, for example, in the form of steam credits for other processes.

Use of the process of this aspect of the present invention for the oxidative dehydrogenation of alkanes results in a conversion rate of alkanes of at least 40%, more preferably at least 50% and still more preferably at least 60%. Further an alkene selectivity of at least 40%, more preferably at least 50% and still more preferably at least 60% is observed.

Turning to the second aspect of the present invention, there is provided a method for producing an unsaturated carboxylic acid that comprises contacting, in a reaction zone, a feed gas stream comprising an alkane with a catalyst system comprising a first catalyst component and a second catalyst component. The first catalyst component is capable of catalyzing the conversion of an alkane to a product comprising a corresponding product alkene and unreacted alkane. The second catalyst component is capable of catalyzing the conversion of an alkane to a product comprising a corresponding product unsaturated carboxylic acid and capable of catalyzing the conversion of an alkene to a product comprising a corresponding product unsaturated carboxylic acid. The first catalyst component is different from the second catalyst component. (In regard to the above, a "corresponding product alkene" means an alkene, i.e. a mono-olefin, having the same number of carbon atoms as the starting alkane. Similarly, a "corresponding product unsaturated carboxylic acid" means an α,β-unsaturated carboxylic acid having the same number of carbon atoms as the starting alkane or alkene (mono-olefin).)

In one embodiment, the first catalyst component and the second catalyst component are mixed together. In this embodiment, catalysts suitable for the conversion of an alkane to an alkene include, for example, promoted MoVNb oxides, vanadyl pyrophosphate and other oxidative dehydrogenation catalysts as described, for example, in U.S. Pat. Nos. 4,148,757, 4,212,766, 4,260,822 and 5,198,580. Other suitable catalysts include unsupported and SiO2-supported VMgO oxides (Applied Catalysis A: General 208 (2001) 99–110), $MoO_3$/gamma-$Al_2O_3$ catalysts (Applied Catalysis A: General 207 (2001) 421–431), strontium and barium hydroxyapatites (Applied Catalysis A: General 211 (2001) 123–130), $V_2O_5/Y_2O_3$ catalysts (Applied Catalysis A: General 181 (1999) 63–69), K/Mo supported over sol-gel silica-titania mixed oxide catalysts (J. Catalysis 191, 12–29 (2000)), MgVO catalysts (J. Catalysis 158, 452–476 (1996)), vanadyl ion-containing VAPO-5 (vanadium-containing aluminophosphate) and CoAPO-5 (cobalt-containing aluminophosphate) catalysts (J. Catalysis 192, 128–136 (2000)), $Ni_xMg_{1-x}Al_2O_4$ and $NiCr_2O_4$ spinels (J. Catalysis 187, 410–418 (1999)), $Nb_2O_5$ supported $V_2O_5$ catalysts (Catalysis Today 28, 139–145 (1996)), metal molybdates (Catalysis Today 24, 327–333 (1995)), rare-earth-oxide (REO)-based catalysts (Catalysis Today 62, 91–99 (2000)) and zeolites modified with a Group 1A modifier and containing a transition metal component (U.S. Pat. No. 5,146,034).

The catalysts suitable for the conversion of an alkane to a product comprising a corresponding product unsaturated carboxylic acid and being suitable for the conversion of an alkene to a product comprising a corresponding product unsaturated carboxylic acid include, for example, mixed metal oxides as disclosed in U.S. Pat. No. 5,380,933. More particularly, the second catalyst component comprises a mixed metal oxide having the empirical formula $$A_aM_bN_cX_dO_e$$

wherein A is at least one element selected from the group consisting of Mo and W, M is at least one element selected from the group consisting of V, Ce and Cr, N is at least one element selected from the group consisting of Te, Bi, Sb and Se, X is at least one element selected from the group consisting of Nb, Ta, Ti, Al, Zr, Mn, Fe, Ru, Co, Rh, Ni, Pt, B, In, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb and Lu; and wherein, when a=1, b=0.01 to 1.0, c=0.01 to 1.0, d=0.01 to 1.0, e is dependent on the oxidation state of the other elements.

Preferably, when a=1, b=0.1 to 0.5, c=0.05 to 0.5 and d=0.01 to 0.5. More preferably, when a=1, b=0.15 to 0.45, c=0.05 to 0.45 and d=0.01 to 0.1. The value of e, i.e. the amount of oxygen present, is dependent on the oxidation state of the other elements in the catalyst. However, e is typically in the range of from 3 to 4.7.

Preferred promoted mixed metal oxides have the empirical formulae $Mo_aV_bTe_cNb_dO_e$ and $W_aV_bTe_cNb_dO$ wherein a, b, c, d and e are as previously defined.

Further, as the mixed metal oxide, one having a certain specific crystal structure is preferred. Specifically, preference is given to the one which exhibits the following five main diffraction peaks at specific diffraction angles 2θ in the X-ray diffraction pattern of the promoted mixed metal oxide (as measured using Cu—Kα radiation as the source):

| X-ray lattice plane | | |
|---|---|---|
| Diffraction angle 2θ (±0.3°) | Spacing medium  (Å) | Relative intensity |
| 22.1° | 4.02 | 100 |
| 28.2° | 3.16 | 20~150 |
| 36.2° | 2.48 | 5~60 |
| 45.2° | 2.00 | 2~40 |
| 50.0° | 1.82 | 2~40 |

The intensity of the X-ray diffraction peaks may vary upon the measuring of each crystal. However, the intensity, relative to the peak intensity at 22.1° being 100, is usually within the above ranges. Generally, the peak intensities at 2θ=22.1° and 28.2° are distinctly observed. However, so long as the above five diffraction peaks are observable, the basic-crystal structure is the same even if other peaks are observed in addition to the five diffraction peaks, and such a structure is useful for the present invention. The mixed metal oxide can be prepared in the following manner.

In a first step a slurry or solution may be formed by admixing metal compounds, preferably at least one of which contains oxygen, and at least one solvent in appropriate amounts to form the slurry or solution. Preferably, a solution is formed at this stage of the catalyst preparation. Generally, the metal compounds contain elements A, M, N, X and O, as previously defined.

Suitable solvents include water; alcohols including, but not limited to, methanol, ethanol, propanol, and diols, etc.; as well as other polar solvents known in the art. Generally, water is preferred. The water is any water suitable for use in chemical syntheses including, without limitation, distilled water and de-ionized water. The amount of water present is preferably an amount sufficient to keep the elements substantially in solution long enough to avoid or minimize compositional and/or phase segregation during the preparation steps. Accordingly, the amount of water will vary according to the amounts and solubilities of the materials combined. However, as stated above, the amount of water is preferably sufficient to ensure an aqueous solution is formed at the time of mixing.

For example, when a mixed metal oxide of the formula $Mo_aV_bTe_cNb_dO_e$ wherein the element A is Mo, the element M is V, the element N is Te and the element X is Nb, is to be prepared, an aqueous solution of niobium oxalate may be added to an aqueous solution or slurry of ammonium heptamolybdate, ammonium metavanadate and telluric acid, so that the atomic ratio of the respective metal elements would be in the prescribed proportions.

Once the aqueous slurry or solution (preferably a solution) is formed, the water is removed by any suitable method, known in the art, to form a catalyst precursor. Such methods include, without limitation, vacuum drying, freeze drying, spray drying, rotary evaporation and air drying. Vacuum drying is generally performed at pressures ranging from 10 mm Hg to 500 mm Hg. Freeze drying typically entails freezing the slurry or solution, using, for instance, liquid nitrogen, and drying the frozen slurry or solution under vacuum. Spray drying is generally performed under inert atmosphere such as nitrogen or argon, with an inlet temperature ranging from 125° C. to 200° C. and an outlet temperature ranging from 75° C. to 150° C. Rotary evaporation is generally performed at a bath temperature of from 25° C. to 90° C. and at a pressure of from 10 mm Hg to 760 mm Hg, preferably at a bath temperature of from 40° to 90° C. and at a pressure of from 10 mm Hg to 350 mm Hg, more preferably at a bath temperature of from 40° C. to 60° C. and at a pressure of from 10 mm Hg to 40 mm Hg. Air drying may be effected at temperatures ranging from 25° C. to 90° C. Rotary evaporation or air drying are generally preferred.

Once obtained, the catalyst precursor is calcined. The calcination may be conducted in an oxygen-containing atmosphere or in the substantial absence of oxygen, e.g., in an inert atmosphere or in vacuo. The inert atmosphere may be any material which is substantially inert, i.e., does not react or interact with, the catalyst precursor. Suitable examples include, without limitation, nitrogen, argon, xenon, helium or mixtures thereof. Preferably, the inert atmosphere is argon or nitrogen. The inert atmosphere may flow over the surface of the catalyst precursor or may not flow thereover (a static environment). When the inert atmosphere does flow over the surface of the catalyst precursor, the flow rate can vary over a wide range, e.g., at a space velocity of from 1 to 500 hr$^{-1}$.

The calcination is usually performed at a temperature of from 350° C. to 850° C., preferably from 400° C. to 700° C., more preferably from 500° C. to 640° C. The calcination is performed for an amount of time suitable to form the aforementioned catalyst. Typically, the calcination is performed for from 0.5 to 30 hours, preferably from 1 to 25 hours, more preferably for from 1 to 15 hours, to obtain the desired promoted mixed metal oxide.

In a preferred mode of operation, the catalyst precursor is calcined in two stages. In the first stage, the catalyst precursor is calcined in an oxidizing environment (e.g. air) at a temperature of from 200° C. to 400° C., preferably from 275° C. to 325° C. for from 15 minutes to 8 hours, preferably for from 1 to 3 hours. In the second stage, the material from the first stage is calcined in a non-oxidizing environment (e.g., an inert atmosphere) at a temperature of from 500° C. to 750° C., preferably for from 550° C. to 650° C., for 15 minutes to 8 hours, preferably for from 1 to 3 hours. Optionally, a reducing gas, such as, for example, ammonia or hydrogen, may be added during the second stage calcination.

In a particularly preferred mode of operation, the catalyst precursor in the first stage is placed in-the desired oxidizing atmosphere at room temperature and then raised to the first stage calcination temperature and held there for the desired first stage calcination time. The atmosphere is then replaced with the desired non-oxidizing atmosphere for the second stage calcination, the temperature is raised to the desired second stage calcination temperature and held there for the desired second stage calcination time.

Although any type of heating mechanism, e.g., a furnace, may be utilized during the calcination, it is preferred to conduct the calcination under a flow of the designated gaseous environment. Therefore, it is advantageous to conduct the calcination in a bed with continuous flow of the desired gas(es) through the bed of solid catalyst precursor particles.

With calcination, a catalyst is formed having the formula $A_aM_bN_cX_dO_e$ wherein A, M, N, X, O, a, b, c, d and e are as previously defined.

The starting materials for the above promoted mixed metal oxide are not limited to those described above. A wide range of materials including, for example, oxides, nitrates, halides or oxyhalides, alkoxides, acetylacetonates, and organometallic compounds may be used. For example, ammonium heptamolybdate may be utilized for the source of molybdenum in the catalyst. However, compounds such as $MoO_3$, $MoO_2$, $MoCl_5$, $MoOCl_4$, $Mo(OC_2H_5)_5$, molybdenum acetylacetonate, phosphomolybdic acid and silicomolybdic acid may also be utilized instead of ammonium heptamolybdate. Similarly, ammonium metavanadate may be utilized for the source of vanadium in the catalyst. However, compounds such as $V_2O_5$, $V_2O_3$, $VOCl_3$, $VCl_4$, $VO(OC_2H_5)_3$, vanadium acetylacetonate and vanadyl acetylacetonate may also be utilized instead of ammonium metavanadate. The tellurium source may include telluric acid, $TeCl_4$, $Te(OC_2H_5)_5$, $Te(OCH(CH_3)_2)_4$ and $TeO_2$. The niobium source may include ammonium niobium oxalate, $Nb_2O_5$, $NbCl_5$, niobic acid or $Nb(OC_2H_5)_5$ as well as the more conventional niobium oxalate.

A mixed metal oxide, thus obtained, exhibits excellent catalytic activities by itself. However, the promoted mixed metal oxide may be converted to a catalyst having higher activities by grinding.

There is no particular restriction as to the grinding method, and conventional methods may be employed. As a dry grinding method, a method of using a gas stream grinder may, for example, be mentioned wherein coarse particles are permitted to collide with one another in a high speed gas stream for grinding. The grinding may be conducted not only mechanically but also by using a mortar or the like in the case of a small scale operation.

As a wet grinding method wherein grinding is conducted in a wet state by adding water or an organic solvent to the above mixed metal oxide, a conventional method of using a rotary cylinder-type medium mill or a medium-stirring type mill, may be mentioned. The rotary cylinder-type medium mill is a wet mill of the type wherein a container for the object to be ground is rotated, and it includes, for example, a ball mill and a rod mill. The medium-stirring type mill is a wet mill of the type wherein the object to be ground, contained in a container is stirred by a stirring apparatus, and it includes, for example, a rotary screw type mill, and a rotary disc type mill.

The conditions for grinding may suitably be set to meet the nature of the above-mentioned promoted mixed metal oxide, the viscosity, the concentration, etc. of the solvent used in the case of wet grinding, or the optimum conditions of the grinding apparatus. However, it is preferred that grinding is conducted until the average particle size of the ground catalyst precursor would usually be at most 20 $\mu$m, more preferably at most 5 $\mu$m. Improvement in the catalytic performance may occur due to such grinding.

Further, in some cases, it is possible to further improve the catalytic activities by further adding a solvent to the ground catalyst precursor to form a solution or slurry, followed by drying again. There is no particular restriction as to the concentration of the solution or slurry, and it is usual to adjust the solution or slurry so that the total amount of the starting material compounds for the ground catalyst precursor is from 10 to 60 wt %. Then, this solution or slurry is dried by a method such as spray drying, freeze drying, evaporation to dryness or vacuum drying, preferably by the spray drying method. Further, similar drying may be conducted also in the case where wet grinding is conducted.

The oxide obtained by the above-mentioned method may be used as a final catalyst, but it may further be subjected to heat treatment usually at a temperature of from 200° to 700° C. for from 0.1 to 10 hours.

The promoted mixed metal oxide thus obtained may be used by itself as a solid catalyst, but may be formed into a catalyst together with a suitable carrier such as silica, alumina, titania, aluminosilicate, diatomaceous earth or zirconia. Further, it may be molded into a suitable shape and particle size depending upon the scale or system of the reactor.

Alternatively, the metal components of the presently contemplated catalyst may be supported on materials such as alumina, silica, silica-alumina, zirconia, titania, etc. by conventional incipient wetness techniques. In one typical method, solutions containing the metals are contacted with the dry support such that the support is wetted; then, the resultant wetted material is dried, for example, at a temperature from room temperature to 200° C. followed by calcination as described above. In another method, metal solutions are contacted with the support, typically in volume ratios of greater than 3:1 (metal solution: support), and the solution agitated such that the metal ions are ion-exchanged onto the support. The metal-containing support is then dried and calcined as detailed above.

In the production of an unsaturated carboxylic acid, it is preferred to employ a starting material gas which contains steam. In such a case, as a starting material gas to be supplied to the reaction system, a gas mixture comprising a steam-containing alkane and an oxygen-containing gas, is usually used. However, the steam-containing alkane and the oxygen-containing gas may be alternately supplied to the reaction system. The steam to be employed may be present in the form of steam gas in the reaction system, and the manner of its introduction is not particularly limited.

Further, as a diluting gas, an inert gas such as carbon dioxide, nitrogen, argon or helium may be supplied. The molar ratio (alkane): (oxygen): (diluting gas): ($H_2O$) in the starting material gas is preferably (1):(0.1 to 10):(0 to 20):(0.2 to 70), more preferably (1):(1 to 5.0):(0 to 10):(5 to 40).

When steam is supplied together with the alkane as starting material gas, the selectivity for an unsaturated carboxylic acid is distinctly improved, and the unsaturated carboxylic acid can be obtained from the alkane, in good yield simply by contacting in one stage. However, the conventional technique utilizes a diluting gas such as nitrogen, argon or helium for the purpose of diluting the starting material. As such a diluting gas, to adjust the space velocity, the oxygen partial pressure and the steam partial pressure, an inert gas such as nitrogen, argon or helium may be used together with the steam.

As the starting material alkane it is preferred to employ a $C_{3-8}$alkane, particularly propane, isobutane or n-butane; more preferably, propane or isobutane; most preferably, propane. According to the present invention, from such an alkane, an unsaturated carboxylic acid such as an α,β-unsaturated carboxylic acid can be obtained in good yield. For example, when propane or isobutane is used as the starting material alkane, acrylic acid or methacrylic acid will be obtained, respectively, in good yield.

As an alternative, an alkanol, such as isobutanol or t-butanol, which will dehydrate under the reaction conditions to form its corresponding alkene, i.e. isobutene, may also be used as a feed to the present process or in conjunction with the previously mentioned feed streams.

The purity of the starting material alkane is not particularly limited, and an alkane containing a lower alkane such as methane or ethane, air or carbon dioxide, as impurities, may be used without any particular problem. Further, the starting material alkane may be a mixture of various alkanes or a mixture of alkane and alkene.

The detailed mechanism of the oxidation reaction of the present invention is not clearly understood, but the oxidation reaction is carried out by oxygen atoms present in the above mixed metal oxide or by molecular oxygen present in the feed gas. To incorporate molecular oxygen into the feed gas, such molecular oxygen may be pure oxygen gas. However, it is usually more economical to use an oxygen-containing gas such as air, since purity is not particularly required.

It is also possible to use only an alkane substantially in the absence of molecular oxygen for the vapor phase catalytic reaction. In such a case, it is preferred to adopt a method wherein a part of the catalyst is appropriately withdrawn from the reaction zone from time to time, then sent to an oxidation regenerator, regenerated and then returned to the reaction zone for reuse. As the regeneration method of the catalyst, a method may, for example, be mentioned which comprises contacting an oxidative gas such as oxygen, air or nitrogen monoxide with the catalyst in the regenerator usually at a temperature of from 300° to 600° C.

This embodiment of the second aspect of the present invention will be described in further detail with respect to a case where propane is used as the starting material alkane and air is used as the oxygen source. The reaction system may be a fixed bed system or a fluidized bed system. However, since the reaction is an exothermic reaction, a fluidized bed system may preferably be employed whereby it is easy to control the reaction temperature. The proportion of air to be supplied to the reaction system is important for the selectivity for the resulting acrylic acid, and it is usually at most 25 moles, preferably from 0.2 to 18 moles per mole of propane, whereby high selectivity for acrylic acid can be obtained. This reaction can be conducted usually under atmospheric pressure, but may be conducted under a slightly elevated pressure or slightly reduced pressure. With respect to other alkanes such as isobutane, the composition of the feed gas may be selected in accordance with the conditions for propane.

Typical reaction conditions for the oxidation of propane or isobutane to acrylic acid or methacrylic acid may be utilized in the practice of the present invention. The process may be practiced in a single pass mode (only fresh feed is fed to the reactor) or in a recycle mode (at least a portion of the reactor effluent is returned to the reactor). General conditions for the process of the present invention are as follows: the reaction temperature can vary from 200° C. to 700° C., but is usually in the range of from 200° C. to 550° C., more preferably 250° C. to 480° C., most preferably 300° C. to 400°; the gas space velocity, SV, in the vapor phase reactor is usually within a range of from 100 to 10,000 $hr^{-1}$, preferably 300 to 6,000 $hr^{-1}$, more preferably 300 to 2,000 $hr^{-1}$; the average contact time with the catalyst can be from 0.01 to 10 seconds or more, but is usually in the range of from 0.1 to 10 seconds, preferably from 2 to 6 seconds; the pressure in the reaction zone usually ranges from 0 to 75 psig, but is preferably no more than 50 psig. In a single pass mode process, it is preferred that the oxygen be supplied from an oxygen-containing gas such as air. The single pass mode process may also be practiced with oxygen addition. In the practice of the recycle mode process, oxygen gas by itself is the preferred source so as to avoid the build up of inert gases in the reaction zone.

Of course, in the oxidation reaction of the present invention, it is important that the hydrocarbon and oxygen concentrations in the feed gases be maintained at the appropriate levels to minimize or avoid entering a flammable regime within the reaction zone or especially at the outlet of the reactor zone. Generally, it is preferred that the outlet oxygen levels be low to both minimize after-burning and, particularly, in the recycle mode of operation, to minimize the amount of oxygen in the recycled gaseous effluent stream. In addition, operation of the reaction at a low temperature (below 450° C.) is extremely attractive because after-burning becomes less of a problem which enables the attainment of higher selectivity to the desired products. The catalyst of the present invention operates more efficiently at the lower temperature range set forth above, significantly reducing the formation of acetic acid and carbon oxides, and increasing selectivity to acrylic acid. As a diluting gas to adjust the space velocity and the oxygen partial pressure, an inert gas such as nitrogen, argon or helium may be employed.

When the oxidation reaction of propane is conducted by the method of the present invention, carbon monoxide, carbon dioxide, acetic acid, etc. may be produced as by-products, in addition to acrylic acid. Further, in the method of the present invention, an unsaturated aldehyde may sometimes be formed depending upon the reaction conditions. For example, when propane is present in the starting material mixture, acrolein may be formed; and when isobutane is present in the starting material mixture, methacrolein may be formed. In such a case, such an unsaturated aldehyde can be converted to the desired unsaturated carboxylic acid by subjecting it again to the vapor phase catalytic oxidation with the mixed metal oxide-containing catalyst of the present invention or by subjecting it to a vapor phase catalytic oxidation reaction with a conventional oxidation reaction catalyst for an unsaturated aldehyde.

As a first variant of the first embodiment of the second aspect of the present invention, the catalyst mixture may be prepared in such a manner that the relative proportions of the first catalyst component and the second catalyst component vary in the reaction zone along the path of flow of the reactants. For example, the concentration of the second catalyst component may increase from the inlet of the reaction zone to the outlet of the reaction zone. Such an increase could be in a continuous manner over the length of the reaction zone, or it could take place in incremental steps along the length of the reactor, or a front end of the reactor could have a lower proportion of the second catalyst component and a rear end of the reactor could have a higher proportion of the second catalyst component and an intermediate portion of the reactor could make a transition from the lower to the higher proportions in a continuous manner or incrementally.

As a second variant of the first embodiment of the second aspect of the present invention, the reaction zone may be subdivided into two or more sub-zones, the reaction mixture passing through the sub-zones sequentially. Each of the sub-zones could contain different proportions of the first and second catalyst components, as compared to the other sub-zones. Moreover, within each sub-zone, the relative proportions of the first and second catalyst components could vary in the, manner as described above for the entire reaction zone in the first variant of the first embodiment. For example, the concentration of the second catalyst component could increase in each sub-zone in sequential order.

In a second embodiment of the second aspect of the present invention, the reaction zone may be two or more sub-zones through which the reaction mixture flows sequentially. In this embodiment, one sub-zone can contain the first catalyst component and another sub-zone can contain the second catalyst component. This embodiment offers the advantage that the first catalyst component can desirably include, in addition to the catalytic materials recited as usable as the first catalyst component above, the reducible metal oxide promoted with a Group 8 metal as described with respect to the first aspect of this invention. Moreover, the sub-zone containing such a catalyst can be run as a short contact time reactor, as described with respect to the first aspect of this invention. On the other hand, the sub-zone containing the second catalyst component can be run under the reaction conditions as previously set forth.

In a third embodiment of the second aspect of the present invention, the second catalyst component may be supported on the first catalyst component, for example, by the use of incipient wetness techniques, as previously described. In this embodiment, catalysts suitable for the conversion of an alkane to an alkene (the first catalyst component) include, for example, promoted MoVNb oxides, vanadyl pyrophosphate and other oxidative dehydrogenation catalysts as described, for example, in U.S. Pat. Nos. 4,148,757, 4,212, 766, 4,260,822 and 5,198,580. Other suitable catalysts include unsupported and SiO2-supported VMgO oxides (Applied Catalysis A: General 208 (2001) 99–110), $MoO_3$/ gamma-$Al_2O_3$ catalysts (Applied Catalysis A: General 207 (2001) 421–431), strontium and barium hydroxyapatites (Applied Catalysis A: General 211 (2001) 123–130), $V_2O_5$/ $Y_2O_3$ catalysts (Applied Catalysis A: General 181 (1999) 63–69), K/Mo supported over sol-gel silica-titania mixed oxide catalysts (J. Catalysis 191, 12–29 (2000)), MgVO catalysts (J. Catalysis 158, 452–476 (1996)), vanadyl ion-containing VAPO-5 (vanadium-containing aluminophosphate) and CoAPO-5 (cobalt-containing aluminophosphate) catalysts (J. Catalysis 192, 128–136 (2000)), $Ni_xMg_{1-x}Al_2O_4$ and $NiCr_2O_4$ spinels (J. Catalysis 187, 410–418 (1999)), $Nb_2O_5$ supported $V_2O_5$ catalysts (Catalysis Today 28, 139–145 (1996)), metal molybdates (Catalysis Today 24, 327–333 (1995)), rare-earth-oxide (REO)-based catalysts (Catalysis Today 62, 91–99 (2000)) and zeolites modified with a Group 1A modifier and containing a transition metal component (U.S. Pat. No. 5,146, 034).

The catalysts suitable for the conversion of an alkane to a product comprising a corresponding product unsaturated carboxylic acid and being suitable for the conversion of an alkene to a product comprising a corresponding product unsaturated carboxylic acid (the second catalyst component) include, for example, mixed metal oxides as disclosed in U.S. Pat. No. 5,380,933. More particularly, the second catalyst component comprises a mixed metal oxide having the empirical formula

$$A_aM_bN_cX_dO_e$$

wherein A is at least one element selected from the group consisting of Mo and W, M is at least one element selected from the group consisting of V, Ce and Cr, N is at least one element selected from the group consisting of Te, Bi, Sb and Se, X is at least one element selected from the group consisting of Nb, Ta, Ti, Al, Zr, Mn, Fe, Ru, Co, Rh, Ni, Pt, B, In, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb and Lu; and wherein, when a=1, b=0.01 to 1.0, c=0.01 to 1.0, d=0.01 to 1.0, e is dependent on the oxidation state of the other elements.

As a first variant of the third embodiment of the second aspect of the present invention, the supported catalyst system may be prepared in such a manner that the relative proportions of the first catalyst component and the second catalyst component vary in the reaction zone along the path of flow of the reactants. For example, the concentration of the second catalyst component may increase from the inlet of the reaction zone to the outlet of the reaction zone. Such an increase could be in a continuous manner over the length of the reaction zone, or it could take place in incremental steps along the length of the reactor, or a front end of the reactor could have a lower proportion of the second catalyst component and a rear end of the reactor could have a higher proportion of the second catalyst component and an intermediate portion of the reactor could make a transition from the lower to the higher proportions in a continuous manner or incrementally.

As a second variant of the third embodiment of the second aspect of the present invention, the reaction zone may be subdivided into two or more sub-zones, the reaction mixture passing through the sub-zones sequentially. Each of the sub-zones could contain different proportions of the first and second catalyst components, as compared to the other sub-zones. Moreover, within each sub-zone, the relative proportions of the first and second catalyst components could vary in the manner as described above for the entire reaction zone in the first variant of the third embodiment. For example, the concentration of the second catalyst component could increase in each sub-zone in sequential order.

In the third aspect of the present invention, there is provided a method for producing an unsaturated carboxylic acid that comprises contacting, in a reaction zone, a feed gas stream comprising an alkane with a catalyst system capable of catalyzing the conversion of an alkane to a product gas comprising a product corresponding unsaturated carboxylic acid, a product corresponding alkene and unreacted alkane and being capable of catalyzing the conversion of an alkene to a product gas comprising a product corresponding unsaturated carboxylic acid. The reaction zone comprises at least two sub-zones, with the sub-zones being disposed sequentially. At least one of the sub-zones is maintained at reaction conditions most favorable to the production of the product corresponding alkene, and at least one other sub-zone is maintained at reaction conditions most favorable to the production of the product corresponding unsaturated carboxylic acid. The feed gas passes through the sub-zones in sequential order.

The catalysts suitable for the conversion of an alkane to a product comprising a corresponding product unsaturated carboxylic acid a corresponding product alkene and unreacted alkane, and being suitable for the conversion of an alkene to a product comprising a corresponding product unsaturated carboxylic acid include, for example, mixed metal oxides as disclosed in U.S. Pat. No. 5,380,933. More particularly, the second catalyst component comprises a mixed metal oxide having the empirical formula $$A_aM_bN_cX_dO_e$$

wherein A is at least one element selected from the group consisting of Mo and W, M is at least one element selected from the group consisting of V, Ce and Cr, N is at least one element selected from the group consisting of Te, Bi, Sb and Se, X is at least one element selected from the group consisting of Nb, Ta, Ti, Al, Zr, Mn, Fe, Ru, Co, Rh, Ni, Pt, B, In, As, Ge, Sn, Li, Na, K, Rb, Cs, Fr, Be, Mg, Ca. Sr, Ba, Ra, Hf, Pb, P, Pm, Eu, Gd, Dy, Ho, Er, Tm, Yb and Lu; and wherein, when a=1, b=0.01 to 1.0, c=0.01 to 1.0, d=0.01 to 1.0, e is dependent on the oxidation state of the other elements.

This aspect of the invention offers the advantage that a single catalyst may be utilized, but different sub-zones will provide different reaction conditions for the catalyst. The reaction conditions most favorable to the formation of the product corresponding unsaturated carboxylic acid are set forth above as with respect to the second aspect of this invention, however, they tend to be at the high end of the most preferred temperature range of 300° C. to 400° C., e.g., 380° C. In contrast, the reaction conditions most favorable to the formation of the product corresponding alkene are also as set forth above as with respect to the second aspect of the invention, but, they tend to be at lower temperatures, e.g. 350° C. In any event, the sub-zones should be operated in the most preferred reaction temperature range (300° C. to 400° C.), but they should have a temperature difference between the zones of at least 20° C., preferably 25° C., most preferably 30° C. Moreover, it is further preferred that the lower temperature sub-zone precede the higher temperature sub-zone.

In its fourth aspect, the present invention provides a method for producing an unsaturated nitrile that comprises contacting, in a reaction zone, a feed gas stream comprising an alkane with a catalyst system comprising a first catalyst component and a second catalyst component. The first and second catalyst components may be the same or different. The first catalyst component is capable of catalyzing the conversion of an alkane to a product gas comprising a corresponding product alkene and unreacted alkane. The second catalyst component is capable of catalyzing, in the presence of ammonia, the conversion of an alkane to a product gas comprising a corresponding product unsaturated nitrile and is capable of catalyzing, in the presence of ammonia, the conversion of an alkene to a product gas comprising a corresponding unsaturated nitrile. The reaction zone comprises at least two sub-zones, the sub-zones being disposed sequentially. At least one of the sub-zones contains the first catalyst component and is maintained under reaction conditions favorable to the formation of an alkene. At least one different sub-zone contains the second catalyst component and is maintained under reaction conditions favorable to the formation of an unsaturated nitrile.

In this aspect of the present invention, the first catalyst component includes, for example, promoted MoVNb oxides, vanadyl pyrophosphate and other oxidative dehydrogenation catalysts as described, for example, in U.S. Pat. Nos. 4,148,757, 4,212,766, 4,260,822 and 5,198,580. Other suitable catalysts include unsupported and SiO2-supported VMgO oxides (Applied Catalysis A: General 208 (2001) 99–110), MoO$_3$/gamma-Al$_2$O$_3$ catalysts (Applied Catalysis A: General 207 (2001) 421–431), strontium and barium hydroxyapatites (Applied Catalysis A: General 211 (2001) 123–130), V$_2$O$_5$/Y$_2$O$_3$ catalysts (Applied Catalysis A: General 181 (1999) 63–69), K/Mo supported over sol-gel silica-titania mixed oxide catalysts (J. Catalysis 191, 12–29 (2000)), MgVO catalysts (J. Catalysis 158, 452–476 (1996)), vanadyl ion-containing VAPO-5 (vanadium-containing aluminophosphate) and CoAPO-5 (cobalt-containing aluminophosphate) catalysts (J. Catalysis 192, 128–136 (2000)), Ni$_x$Mg$_{1-x}$Al$_2$O$_4$ and NiCr$_2$O$_4$ spinels (J. Catalysis 187, 410–418 (1999)), Nb$_2$O$_5$ supported V$_2$O$_5$ catalysts (Catalysis Today 28, 139–145 (1996)), metal molybdates (Catalysis Today 24, 327–333 (1995)), rare-earth-oxide (REO)-based catalysts (Catalysis Today 62, 91–99 (2000)) and zeolites modified with a Group 1A modifier and containing a transition metal component (U.S. Pat. No. 5,146,034).

This aspect of the present invention offers the advantage that the first catalyst component can desirably include, in addition to the catalytic materials recited above, the reducible metal oxide promoted with a Group 8 metal as described with respect to the first aspect of this invention. The sub-zone containing such a catalyst can be run as a short contact time reactor as described with respect to the first aspect of this invention.

Moreover, this aspect of the present invention also offers the advantage that the first catalyst component can desirably include mixed metal oxides as disclosed in U.S. Pat. No. 5,380,933. More particularly, the first catalyst component may comprise a mixed metal oxide having the empirical formula $$A_aM_bN_cX_dO_e$$

wherein A is at least one element selected from the group consisting of Mo and W, M is at least one element selected from the group consisting of V, Ce and Cr, N is at least one element selected from the group consisting of Te, Bi, Sb and Se, X is at least one element selected from the group consisting of Nb, Ta, Ti, Al, Zr, Mn, Fe, Ru, Co, Rh, Ni, Pt, B, In, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb and Lu; and
    wherein, when a=1, b=0.01 to 1.0, c=0.01 to 1.0, d=0.01 to 1.0, e is dependent on the oxidation state of the other elements. The sub-zone containing such a catalyst can be run under reaction conditions favorable to the formation of an alkene, as described above.

The second catalyst component includes mixed metal oxides as disclosed in U.S. Pat. No. 5,380,933. More particularly, the second catalyst component may comprise a mixed metal oxide having the empirical formula $$A_a M_b N_c X_d O_e$$

wherein A is at least one element selected from the group consisting of Mo and W, M is at least one element selected from the group consisting of V, Ce and Cr, N is at least one element selected from the group consisting of Te, Bi, Sb and Se, X is at least one element selected from the group consisting of Nb, Ta, Ti, Al, Zr, Mn, Fe, Ru, Co, Rh, Ni, Pt, B, In, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb and Lu; and
wherein, when a=1, b=0.01 to 1.0, c=0.01 to 1.0, d=0.01 to 1.0, e is dependent on the oxidation state of the other elements.

In the production of an unsaturated nitrile, as the starting material alkane, it is preferred to employ a $C_{3-8}$ alkane such as propane, butane, isobutane, pentane, hexane and heptane. However, in view of the industrial application of nitrites to be produced, it is preferred to employ a lower alkane having 3 or 4 carbon atoms, particularly propane and isobutane.

The purity of the starting material alkane is not particularly limited, and an alkane containing a lower alkane such as methane or ethane, air or carbon dioxide, as impurities, may be used without any particular problem. Further, the starting material alkane may be a mixture of various alkanes.

The detailed mechanism of the ammoxidation reaction of this aspect of the present invention is not clearly understood. However, the oxidation reaction is conducted by the oxygen atoms present in the above promoted mixed metal oxide or by the molecular oxygen in the feed gas. When molecular oxygen is incorporated in the feed gas, the oxygen may be pure oxygen gas. However, since high purity is not required, it is usually economical to use an oxygen-containing gas such as air.

As the feed gas, it is possible to use a gas mixture comprising the product gas emerging from the sub-zone containing the first catalyst component, ammonia and an oxygen-containing gas, However, a gas mixture comprising the product gas emerging from the sub-zone containing the first catalyst component and ammonia, and an oxygen-containing gas may be supplied alternately.

When the gas phase catalytic reaction is conducted using the product gas emerging from the sub-zone containing the first catalyst component and ammonia substantially free from molecular oxygen, as the feed gas, it is advisable to employ a method wherein a part of the catalyst is periodically withdrawn and sent to an oxidation regenerator for regeneration, and the regenerated catalyst is returned to the sub-zone. As a method for regenerating the catalyst, a method may be mentioned wherein an oxidizing gas such as oxygen, air or nitrogen monoxide is permitted to flow through the catalyst in the regenerator usually at a temperature of from 300° C. to 600° C.

The fourth aspect of the present invention will now be described in further detail. The proportion of air to be supplied for the reaction is important with respect to the selectivity for the resulting acrylonitrile. Namely, high selectivity for acrylonitrile is obtained when air is supplied within a range of at most 25 moles, particularly 1 to 15 moles, per mole of the hydrocarbon in the product gas emerging from the sub-zone containing the first catalyst component. The proportion of ammonia to be supplied for the reaction is preferably within a range of from 0.2 to 5 moles, particularly from 0.5 to 3 moles, per mole of the hydrocarbom. This reaction may usually be conducted under atmospheric pressure, but may be conducted under a slightly increased pressure or a slightly reduced pressure.

The reactor conditions for the sub-zone wherein unsaturated nitrile is formed in the fourth aspect of the present invention include a temperature of, for example, from 250° C. to 480° C. More preferably, the temperature is from 300° C. to 400° C. The gas space velocity, SV, in the gas phase reaction is usually within the range of from 100 to 10,000 $hr^{-1}$, preferably from 300 to 6,000 $hr^{-1}$, more preferably from 300 to 2,000 $hr^{-1}$. As a diluent gas, for adjusting the space velocity and the oxygen partial pressure, an inert gas such as nitrogen, argon or helium can be employed. When ammoxidation is conducted by the method of the present invention and propane is utilized as the initial alkane feed, in addition to acrylonitrile, carbon monoxide, carbon dioxide, acetonitrile, hydrocyanic acid and acrolein may form as by-products.

EXAMPLES

Example 1

Catalyst Preparation

Catalyst A

Ceramic foam monoliths (disks: 10 mm thick, 18 mm in diameter) made of Mg-stabilized $ZrO_2$ from Vesuvius Hi-Tech Ceramics with 80 pores per linear inch (ppi) were impregnated with a solution of chromium nitrate ($Cr(NO_3)_3 \cdot 9H_2O$, 0.224 g, from Aldrich) and copper nitrate ($Cu(NO_3)_2 \cdot 2.5H_2O$, 0.013 g, from Aldrich) in deionized water (0.8 g). The resulting material was dried in a vacuum oven at 70° C. over night and calcined in air at 600° C. for 4 hours. This preparation resulted in loadings of approximately 5 wt % $CuO/Cr_2O_3$ (Cr:Cu=10:1) on the $ZrO_2$ monolith.

Catalyst B

Ceramic foam monoliths (disks: 10 mm thick, 18 mm in diameter) made of Mg-stabilized $ZrO_2$ from Vesuvius Hi-Tech Ceramics with 80 pores per linear inch (ppi) were impregnated with a solution of chromium nitrate ($Cr(NO_3)_3 \cdot 9H_2O$, 0.224 g, from Aldrich) and copper nitrate ($Cu(NO_3)_2 \cdot 2.5H_2O$, 0.013 g, from Aldrich) in deionized water (0.8 g) mixed with 0.164 g of aqueous solution of hydrogen hexachloroplatinate(IV) (8 wt % from Aldrich). The resulting material was dried in a vacuum oven at 70° C. over night and calcined in air at 600° C. for 4 hours. This preparation resulted in loadings of approximately 5 wt % $CuO/Cr_2O_3$ (Cr:Cu=10:1) and 1 wt % Pt oxide on the $ZrO_2$ monolith.

Reaction

For each of the catalysts A and B, a 33 to 38 cm long quartz tube with an inner diameter of 22 mm was provided. A cylindrical foam monolith support structure coated with a catalyst as described further herein and having a diameter of 18 mm and thickness of 10 mm was placed between two inert, uncoated foam monoliths (heat shields) and sealed in the tube with high temperature silica-alumina felt, which prevented the by-pass of reactants around the catalyst and thermally insulated the catalyst, i.e. the heat shields in front and behind the catalyst reduced the radiative heat loss from the catalyst in the axial direction. During reaction, the front heat shield was heated by the catalyst and served to preheat the reactants before they reached the catalyst.

The outside of the reactor was also covered with insulation, a 0.8 to 2.5 cm thick pad of silica-alumina felt, that extended 2 cm beyond the edge of the heat shields to reduce heat losses in the radial direction. The reactor tube was connected to a gas handling system by metal compression fittings with a Viton O-ring that formed the seal between the quartz reactor tube and the metal compression fittings. The reactor tube with these compression connections was connected to the process tubing by Quick-connect clamps and flange-swage connections.

The gas flow for the reactor was controlled by Brooks 5850E electronic mass flow controllers with an accuracy of ±0.06 standard liter per minute (SPLM) for each component. The total feed flow was 2 SLPM, which corresponded to a contact time of 2 milliseconds. For all experiments, the reactor pressure was maintained at 1.2 atm (18 psi). The reaction occurred autothermally at 500° C. and a sample of the product gases was fed to an HP 6890 Gas Chromatograph (GC) through heated stainless steel lines.

While the reaction operates autothermally at steady state, an external heat source was used to ignite the reaction. The gas mixture ignited at approximately 300° C. over the catalysts at a flow of 2 SLPM. After ignition, the external heat source was removed. The feed gas consisted of propane and $O_2$ with $N_2$ as a diluent (propane: $O_2:N_2$=34.4:15.6:50). The $N_2$ also served as an internal GC calibration. All species concentrations except $H_2O$ were measured relative to GC calibration standards. The $H_2O$ concentration was calculated by an oxygen atom balance. The remaining atom balances, carbon and hydrogen, closed to within ±2%.

The reaction temperature was measured by a type K (chrome/alumel) thermocouple inserted from the rear of the reactor and placed at the center of the reactor between the catalyst and the rear radiation heat shield.

The results are set forth in Table 1.

TABLE 1

| Catalyst | Pt (wt %) | Temp (° C.) | % Propane Conversion | % Propene Selectivity |
| --- | --- | --- | --- | --- |
| A | 0 | 900 | 50 | 50 |
| B | 1.1 | 500 | 64 | 61 |

The results set forth in Table 1 demonstrate the benefit of adding promoter amounts of the Group 8 metal to the reducible metal oxide catalyst. The autothermal run temperature decreased by 400° C. while the propane conversion and the propene selectivity both increased substantially.

Example 2

In a flask containing 215 g of water, 25.68 g of ammonium heptamolybdate tetrahydrate (Aldrich Chemical Company), 5.06 g of ammonium metavanadate (Alfa-Aesar) and 7.68 g of telluric acid (Aldrich Chemical Company) were dissolved upon heating to 70° C. After cooling to 40° C., 2.84 g of oxalic acid (Aldrich Chemical Company) was dissolved in 122.94 g of an aqueous solution of niobium oxalate (H. C. Starck) containing 1.25% Nb. This was then addee to the three component mixture to obtain a solution. The water of this solution was removed via a rotary evaporator (water bath at 50° C., vacuum pressure of 28 mm Hg) to obtain 46 g of precursor solid. 23 g of this catalyst precursor solid was calcined in a quartz tube heated to 275° C. at 10° C./min with a 100 cc/min flow of air through the tube and held for one hour, then using a 100 cc/min flow of argon, ramped to 600° C. at 2° C./min and held for 2 hours. The catalyst thus obtained was pressed in a mold and then broken and sieved to 10–20 mesh granules. Ten grams of the granules were packed into a 1.1 cm inside diameter stainless steel U-tube reactor for gas phase propane oxidation. The oxidation was conducted with a reactor bath (molten salt) temperature of 380° C., a 3 second residence time, a feed ratio of propane/air/steam of 1/15/14, and a space velocity of 1,200 $hr^{-1}$. The effluent of the reactor was condensed to separate the liquid phase (the condensable material) and the gas phase. The gas phase was analyzed by gas chromatography (GC) to determine the propane conversion. The liquid phase was also analyzed by GC for the yield of acrylic acid (AA). The results are shown in Table 2.

Example 3

An amount of 200 mL of distilled water, in a 400 mL beaker, was heated, while stirring, until the temperature reached 70–75° C. Then, 0.16 g of $NH_4VO_3$ (Fisher ACS grade) and 0.63 g of $Zn(NO_3)_2 \cdot 6H_2O$ (Aldrich 98%) were added one-by-one. These were dissolved completely before 14.71 g of gamma-$Al_2O_3$ was added in small portions. The liquid phase was evaporated while stirring until a thick paste remained. The resulting paste was transferred to a ceramic dish and dried in air at 110° C. for 9 hours and then calcined in air at 650° C. for 5 hours. The resulting material had 2 wt % $Zn_3(VO_4)_2$ supported on gamma-$Al_2O_3$ and performed as set forth in Table 2.

Example 4

The calcined mixed metal oxide of Example 2 was combined with the 2 wt % $Zn_3(VO_4)_2$ supported on gamma-$Al_2O_3$ of Example 3 to give a mixture of 95% mixed metal oxide and 5% of the oxidative dehydrogenation catalyst (i.e. the 2 wt % $Zn_3(VO_4)_2$ supported on gamma-$Al_2O_3$). Mixing was conducted in a mortar and pestle for 5 minutes. The ground mixture thus obtained was pressed in a mold and then broken and sieved to 10–20 mesh granules. Ten grams of the granules were packed into a 1.1 cm inside diameter stainless steel U-tube reactor for gas phase propane oxidation. The oxidation was conducted with a reactor bath (molten salt) temperature of 380° C., a 3 second residence time, a feed ratio of propane/air/steam of 1/15/14, and a space velocity of 1,200 $hr^{-1}$. The effluent from the reactor was condensed to separate the liquid phase (the condensable material) and the gas phase. The gas phase was analyzed by gas chromatography (GC) to determine the propane conversion. The liquid phase was analyzed by GC for the yield of acrylic acid (AA). The results are shown in Table 2.

TABLE 2

| Example | % Propane Conversion | % AA Yield |
| --- | --- | --- |
| 3 | 17 | 12 |
| 4 | 1 | 0 |
| 5 | 36 | 23 |

Compared to the mixed metal oxide alone, data in Table 2 indicate increases in propane conversion and AA yield occur with the mixture of the mixed metal oxide combined with the oxidative dehydrogenation catalyst, i.e. 2 wt % $Zn_3(VO_4)_2$ supported on gamma-$Al_2O_3$. The oxidative dehydrogenation catalyst (2 wt % $Zn_3(VO_4)_2$ supported on gamma-$Al_2O_3$) alone was essentially inactice in propane conversion at these run conditions.

What is claimed is:

1. A method for producing an alkene consisting of 3–8 carbons, said method comprising:
   a. providing a three-dimensional support structure for supporting a catalyst;

b. providing a catalyst on at least a portion of said support structure, said catalyst comprising a reducible metal oxide promoted with a Group 8 promoter metal;

c. reacting an alkane with oxygen in the presence of said supported catalyst, said reaction having a contact time of no longer than 100 milliseconds and providing a conversion rate of said alkane of at least 40%.

2. The method according to claim 1, wherein said three-dimensional support structure is selected from the group consisting of foam, honeycomb, lattice, mesh, monolith, woven fiber, non-woven fiber, gauze, perforated foil, particle compacts, fibrous mat and mixtures thereof.

3. The method according to claim 1, wherein said support structure is fabricated from a material selected from the group consisting of silica, alumina, silica-alumina, aluminosilicate, zirconia, titania, boria, mullite, lithium aluminum silicate, oxide-bonded silicon carbide and mixtures thereof.

4. The method according to claim 1, wherein said reducible metal oxide is an oxide of a metal selected from the group consisting of Cu, Cr, V, Mn, Nb, Mo, W, Re, Ga, Ge, In, Sn, Sb, Tl, Pb, Bi, Te, As, Se, Zn, Y, Zr, Ta, Ce, Pr, Nd, Pm, Sm, Eu, Gd, Tb, Dy, Ho, Er, Tm, Yb, Lu and mixtures thereof.

5. The method according to claim 1, wherein said Group 8 promoter metal is selected from the group consisting of Pt, Pd, Rh, Ir, Ru and mixtures thereof.

* * * * *